(12) United States Patent
Andrews et al.

(10) Patent No.: US 6,689,892 B2
(45) Date of Patent: Feb. 10, 2004

(54) PROCESS FOR THE MANUFACTURE OF ANHYDRO SUGAR ALCOHOLS WITH THE ASSISTANCE OF A GAS PURGE

(75) Inventors: Mark Allen Andrews, Wilmington, DE (US); Kamlesh Kumar Bhatia, Newark, DE (US); Paul Joseph Fagan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 95 days.

(21) Appl. No.: 09/864,465

(22) Filed: May 24, 2001

(65) Prior Publication Data

US 2002/0028959 A1 Mar. 7, 2002

Related U.S. Application Data

(60) Provisional application No. 60/207,715, filed on May 26, 2000.

(51) Int. Cl.$^7$ .................. C07D 493/00; C07D 307/02
(52) U.S. Cl. ........................ 549/464; 549/478
(58) Field of Search ................. 549/464, 478

(56) References Cited

U.S. PATENT DOCUMENTS 4,506,086 A * 3/1985 Salzburg et al. ............ 549/464
4,861,513 A * 8/1989 Lueders et al. ............. 549/464

FOREIGN PATENT DOCUMENTS

WO     0014081   *  3/2000  ............. 549/464

* cited by examiner

*Primary Examiner*—Alan L. Rotman
*Assistant Examiner*—Raymond Covington

(57) ABSTRACT

This invention concerns a process for the manufacture of anhydro- and dianhydro- hexitols, pentitols, and tetritols by the dehydration of sugar alcohols (alditols) in the presence of a dehydration catalyst and with the assistance of an inert gas sparge.

14 Claims, 1 Drawing Sheet

PROCESS FOR THE MANUFACTURE OF ANHYDRO SUGAR ALCOHOLS WITH THE ASSISTANCE OF A GAS PURGE

FIELD OF THE INVENTION

This invention concerns a process for the manufacture of anhydro- and dianhydro- hexitols, pentitols, and tetritols by the dehydration of sugar alcohols (alditols) in the presence of a dehydration catalyst and with the assistance of an inert gas sparge.

TECHNICAL BACKGROUND OF THE INVENTION

Anhydro sugar alcohols, in particular derivatives of mannitol, iditol, and sorbitol, are known for their therapeutic uses and uses in food. At least one of these, isosorbide, 1,4:3,6-dianhydrosorbitol, is a monomer useful in the manufacture of polymers and copolymers, especially polyester polymers and copolymers. Isosorbide is a derivative of sorbitol, which can be derived from various natural resources. Sorbitol may be regarded as a renewable natural resource for the manufacture of polymers.

Anhydrosugar alcohols are known to be produced by dehydration of the corresponding sugar alcohols (or monoanhydro sugar alcohols) by the action of various dehydration catalysts, typically strong acids. Examples of these catalysts include sulfonated polystyrenes ($H^+$form) (German Patent DE 3 041 673 C2; Canadian Patent Disclosure CA 1 178 288 A1); and various mineral acids, such as HCl (U.S. Pat. No. 4,169,152; German Patent Disclosure DE 3 233 086 A1), $H_3PO_4$ (East German Patent Disclosure DD 1 32 266; Can. J. Chem., 52 (19) 3362–72 (1974)), HF (International Patent Disclosure WO 89/00162 A; Carbohydr. Res. 205 (1990) 191–202) and $H_2SO_4$ (German Patent Disclosures DE 3 521 809 A1 and DE 3 229 412 A1).

These processes are often performed in the presence of a solvent. As solvents, water (CA 1 178 288 A1; European Patent Disclosure EP 0 052 295 B1) and organic solvents such as toluene or xylene (Przem. Chem. 48 (11) 665–8 (1969)) are known.

Batch processes for the preparation of dianhydro sugar alcohols by acid dehydration have been described in numerous patents and articles, for example, U.S. Pat. No. 3,454,603; 4,564,692; and 4,506,086; Canadian Patent 1178288; and articles J. Am. Chem. Soc., 68(5) pp. 939–941 (1946); J. Chem. Soc., pp. 433–436 (1947); Przem. Chem. 48(11) pp. 665–668 (1969); and Pr. Nauk. Inst. Technol. Org. Tworzyw Sztucznych Politech. Wroclaw. No 3., p. 3–14 (1971).

In particular, a batch process for the formation of the dianhydro sugar alcohol isosorbide has been described in the literature as a two step process involving intramolecular dehydration of sorbitol to sorbitan (1,4-monoanhydro-sorbitol), and further reaction of sorbitan to isosorbide (1,4:3,6-dianhydrosorbitol) in an acid catalyzed dehydration-cyclization. In this process, an aqueous solution of sorbitol is charged to a batch reactor. The temperature is increased to 130° C.–135° C. under vacuum (35 mm Hg) to remove the water. When the sorbitol melt is free of water, a catalyst, usually sulfuric acid, is added and the temperature and vacuum levels are maintained. The operable temperature range of the reaction is very narrow. Higher temperatures lead to decomposition and charring of the end product, while lower temperatures inhibit the reaction rate due to difficulties in removal of the water of reaction. This reaction produces isosorbide and a higher molecular weight by-product. The by-product is presumably produced in part by water elimination between two or more sorbitol molecules, but its exact nature is not clearly defined. See Starch/Starke (1986), 38(c), 26–30 and Roland Beck, Pharm. Mfg Inc. (1996), 97–100. Other monoanhydro by-products, 2,5-anhydro-L-iditol and 2,5-anhydro-D-mannitol, are also known to be produced under some reaction conditions. (Acta. Chem. Scand. B 35, 441–449 (1981)).

International Patent Application WO 00/14081 describes a continuous process for producing anhydro sugar alcohols, especially isosorbide, comprising the steps of introducing at least one sugar alcohol or monoanhydro sugar alcohol into a reaction vessel; dehydrating the sugar alcohol or monoanhydro sugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel.

It is an object of the present invention to provide an improved process for the manufacture of anhydro sugar alcohols, especially isosorbide, by the acid catalyzed dehydration of sugar alcohols that facilitates large scale, economical production without the use of vacuum. One of the salient features of the present invention is the use of an inert gas purge which removes water from the reaction mixture, thereby accelerating the rate of reaction.

SUMMARY OF THE INVENTION

Disclosed is a process for the preparation of a dianhydro sugar alcohol comprising the steps of:

a) introducing to a single vessel a charge of at least one sugar alcohol or monoanhydro sugar alcohol, and optionally, water and, optionally, a dehydration catalyst;

b) contacting said charge with a flow of an inert gas at elevated temperature to remove the bulk of any water present to yield a dewatered process charge;

c) contacting said dewatered process charge with a dehydration catalyst in the presence of a flow of an inert gas at elevated temperatures so as to remove water of reaction as formed.

Disclosed is an apparatus for conducting said process which apparatus comprises a vessel containing a tube which allows the flow of nitrogen through the sorbitol under the conditions of the process. A trap is provided to trap volatilized isosorbide carried with the nitrogen flow.

DETAILED DESCRIPTION OF THE INVENTION

Figure 1:
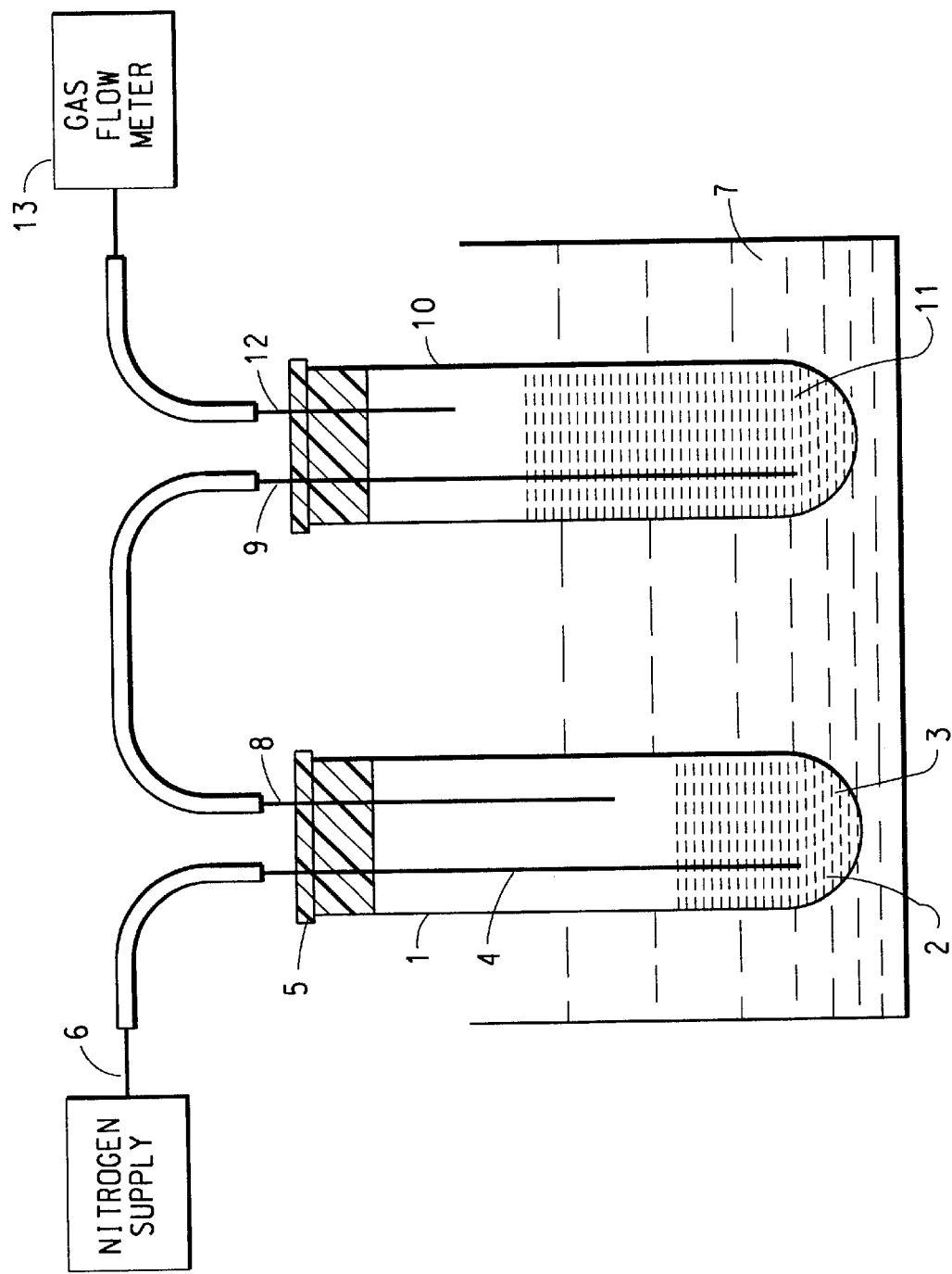
FIG. 1 is a schematic representation of laboratory scale dehydration apparatus utilized in a preferred embodiment of the process of the present invention.

The present disclosure describes a process for the production of anhydro, and dianhydro sugar alcohols, most preferably, a process for the production of isosorbide, 1,4:3, 6-dianhydrosorbitol.

The process is directed toward the production of anhydro- and dianhydro-sugar alcohols and generally includes the steps of introducing at least one sugar alcohol or mono-anhydro sugar alcohol, usually in the form of an aqueous solution, into a reaction vessel in the presence of a flow of an inert gas; removing most of the water from said aqueous solution by evaporation; dehydrating the sugar alcohol or mono-anhydrosugar alcohol in the presence of a catalyst to form a reaction product comprising anhydro- or dianhydro-sugar alcohol and water; removing the water of reaction from said reaction product by evaporation in the presence of a flow of an inert gas; and subsequently removing the reaction product from the reactor for subsequent use or purification.

Optionally, the process may further include an additional purification step.

Typical sugar alcohols, in particular tetritols, pentitols and hexitols, are suitable for use in the process as starting materials. The starting materials may be sugar alcohols, monoanhydro sugar alcohols, or a mixture thereof. In particular, preferred starting materials include erythritol, threitol, xylitol, arabinitol, ribitol, glucitol (also known as -D-sorbitol or sorbitol), mannitol, galactitol, and iditol. The use of sorbitol is most preferred because sorbitol is readily available and can be obtained on a large industrial scale by the reduction of glucose with hydrogen, as known to one of ordinary skill in the art, and the resulting product, isosorbide, is especially valuable for use in the preparation of polyester polymers and copolymers. The preferred form of sorbitol is as its aqueous solution in water, available as an article of commerce as sorbitol, 70%, from Roquette Ferres (Lestram, France), Archer Daniels Midland (Minneapolis, Minn.), SPI Polyols, Cerestar, or, in experimental quantities, from chemical supply houses such as Aldrich (Milwaukee, Wis.).

The catalysts used to facilitate the dehydration reaction are typically strong acid catalysts. Several types of acid catalysts may be used, each having specific advantages and disadvantages. One class of acid catalyst that may be used includes soluble acids. Examples of such acid catalysts include sulfuric acid, phosphoric acid, p-toluene sulfonic acid, methanesulfonic acid and the like. Sulfuric acid is a preferred catalyst from this class.

Alternatively, acid anion exchange resins may also be used, such as sulfonated polystyrenes, for example, AG50W-X12 from BioRad or perfluorinated ion-exchange polymers, such as Nafion®, available from E.I. du Pont de Nemours and Company (Wilmington, Del.). Inorganic ion exchange materials may also be used, for example, acidic zeolites or sulfated metal oxide catalysts.

Preferred acid zeolites are those with a minimum pore dimension (based on ionic radii of the atoms within the zeolite) of greater than or equal to 6.0 Angstroms, and a Si:Al ratio of greater than or equal to 2.8 to 1 and less than or equal to 75:1. Preferred acid zeolites include H-beta zeolite, DA-Y zeolite, H—Y zeolite, H-Mordenite zeolite and H-ZSM-5 zeolite.

Sulfated metal oxide catalysts are those which comprise a single metal ion, or mixtures of metal ions, capable of being sulfated to produce a strongly acidic surface. These compositions are of the type $M^1M^2M^3 \ldots O_x$ ($H_2SO_4$) where $M^1M^2M^3 \ldots O_x$ are mono, binary, ternary (or higher) metal oxide catalysts with supported sulfuric acid. A preferred sulfated metal oxide catalyst is sulfated zirconia.

For the process of the present invention it is preferable to use a soluble catalyst and most preferable is the use of sulfuric acid. In this most preferable mode, sulfuric acid is used such that it comprises 0.1 to 5.0 weight % of the sugar alcohol or anhydrosugar alcohol. The sulfuric acid is supplied to the reactor as an aqueous solution ranging from 1 to 97% sulfuric acid. Acid strength is optimized such that the most concentrated solution of acid results in no detrimental by-product formation at the point of introduction and reduces the overall water removal load on the reaction system.

The dehydration is performed at elevated temperatures between 80 and 180° C., preferably at temperatures between 110 and 160° C., and most preferably at temperatures between 120 and 145° C.

The dehydration is carried out by intimately contacting the reaction mass with a stream of a non-reactive gas, preferably nitrogen. The dehydration is preferably performed at approximately atmospheric pressure, although elevated or reduced pressures can also be used with minor adjustments to other process parameters such as time and temperature. The dehydration catalyst (acid) addition can be performed in such a way that the catalyst is added in the requisite quantity initially, and further catalyst is added on an as-needed basis. However, it is also possible to add the catalyst in continuous fashion during the dehydration reaction.

After dehydration of the starting material is completed, the acid catalyst may be deactivated and/or removed from the reaction product, which preferably has been removed from the reaction vessel. In the case of soluble acid catalysts, the deactivation may be accomplished by any method known in the art, such as addition of a metal oxide or metal hydroxide base to form an insoluble salt. Polymeric ion exchange resins or solid inorganic materials may be recovered by filtration.

Purification of the crude reaction product may occur by distillation, recrystallization, melt recrystallization or a combination thereof. A combination of distillation and recrystallization from an aliphatic alcohol such as methanol or ethanol may be employed in order to minimize the number of purification steps while maximizing the purity of the reaction product. This purification of the reaction product may occur as an additional step coupled to the dehydration process or in a separate process. In either case, the purity of the resultant anhydrosugar alcohol should be at least 99.0%, preferably at least 99.5%, most preferably at least 99.8%, and preferably meets the purity requirements for use in polymer production.

A preferred process of the invention will now be described in relation to FIG. 1.

As shown in FIG. 1, the dehydration takes place in a reaction vessel (1) containing an aqueous solution of sugar alcohol solution (2), acid catalyst (3). The vessel (1) has a nitrogen flow emanating from a tube (4) which extends through a vessel sealing stopper (5) and below the level of the solution to the bottom of the reaction vessel (1). An inert gas is provided from a supply line (6) to the tube (4), and the reaction is heated by lowering the tube into a heat source such as a recirculating oil bath (7) capable of being adjusted to the desired temperature. An outlet tube (8) for the nitrogen is provided and is connected to a tube (9) which enters a water trap vessel (10). The tube (9) is submerged in water (11) contained in the trap (10), and an exit tube (12) is provided that leads to a gas flow meter (13) for measuring and adjusting the gas flow.

The flow of nitrogen entering the reactor (1) from the tube (4) bubbles through the reaction mass and assists in the evaporation of water and any entrained product or organics which are trapped in the water trap (10). The nitrogen flow aids in the removal of water as it is produced in the reaction mixture, thus accelerating the rate of the dehydration of the sugar alcohol.

EXAMPLES

Example 1

Preparation of isosorbide

Weighed amounts of aqueous 70% sorbitol solution were added to 12 separate glass reaction tubes. Each of these reaction tubes was connected to a water trap and set up according to the diagram in FIG. 1. The water trap contained 25 mL of water. Into each reaction tube was injected 483 μL of an aqueous solution containing 0.1075 g of concentrated sulfuric acid. The nitrogen purge into each tube was adjusted to 150 cm³/min. All of the reaction tubes were lowered at once into a 180° C. oil bath. Each tube was pulled from the oil bath at different times as listed in Table 1 to cool and stop the reaction. The mass of the crude remaining in each tube was determined. Small weighed samples of crude material (on the order of 150 mg) from each separate reaction tube were removed and diluted with a weighed amount of 1,9-nonanediol (external standard) contained in approximately 10 mL of anhydrous dimethylacetamide. Approximately 1 mL of each of these solutions was transferred to a gc vial, and treated with 0.150 ml of the silating agent trimethylsilylimidazole in order to determine and quantitate the components in each reaction tube by gas chromatographic analysis. The results of these experiments are presented in Table 1.

Examples 2–10, differing from Example 1 in reaction temperature and time, were conducted according to the same procedure as for Example 1 above. Conditions employed and results obtained are summarized in Table 2.

Examples 11–17 and Comparative Examples 18 to 22, showing the use of different solid acid catalysts, were conducted similarity. Results are in Table 3

Experiment 1. Synthesis of Sulfated Zirconia 500 g zirconium hydroxide (Atomergic Chemetals Corp, Farmingdale N.Y.) was stirred into a solution of 27.5 g ammonium sulfate in 500 mL water. The slurry was stirred for 15 mins then evaporated to dryness on a rotovap. The resulting powder was calcined in flowing air (100 mL/min) at 725° C. for 1 hr then cooled to 500° C. for a further 3 hrs. The calcined white solid was flushed with dry nitrogen and then taken into a nitrogen filled glove box where it was unloaded and stored for testing.

TABLE 1

| Tube # | Sample Time (min) | Temp of oil bath | Internal Rxn Temp. At Stop Time | Sorb Sol Mass (g) | Mass Crude (g) | isosorbide Mole % | mannitol 2,5-anhydro- Mole % | 2,5-anhydro- iditol Mole % | 1,4-anhydro glucitol Mole % | 3,6-anhydro glucitol mole % | sorbitol mole % |
|---|---|---|---|---|---|---|---|---|---|---|---|
| 1 | 6 | 180 | 140 | 25.998 | 20.661 | 0.00 | 0.00 | 0.00 | 0.50 | 0.1 | 101 |
| 2 | 12 | 180 | 165 | 25.999 | 18.289 | 1.45 | 1.63 | 3.96 | 32.1 | 2.51 | 56.4 |
| 3 | 18 | 180 | 170 | 26.016 | 16.588 | 17.7 | 3.92 | 8.93 | 57.6 | 0.7 | 2.36 |
| 4 | 24 | 180 | 174 | 26.000 | 15.468 | 50.4 | 3.71 | 7.41 | 19.6 | 0.1 | 0.1 |
| 5 | 30 | 180 | 178 | 26.016 | 14.945 | 64.6 | 3.43 | 6.02 | 3.17 | 0.00 | 0.1 |
| 6 | 36 | 180 | 180 | 26.019 | 14.253 | 65.2 | 2.22 | 2.41 | 0.1 | 0.00 | 0.00 |
| 7 | 42 | 180 | 180 | 26.000 | 14.278 | 65.2 | 2.11 | 2.14 | 0.2 | 0.00 | 0.00 |
| 8 | 48 | 180 | 180 | 26.010 | 14.276 | 65.7 | 1.91 | 1.71 | 0.1 | 0.00 | 0.3 |
| 9 | 54 | 180 | 180 | 25.998 | 14.052 | 64.3 | 1.58 | 1.12 | 0.0 | 0.00 | 0.00 |
| 10 | 60 | 180 | 180 | 26.011 | 13.956 | 64.0 | 1.43 | 0.90 | 0.1 | 0.00 | 0.2 |
| 11 | 66 | 180 | 180 | 26.014 | 13.706 | 62.6 | 1.27 | 0.69 | 0.1 | 0.00 | 0.00 |
| 12 | 72 | 180 | 181 | 25.996 | 13.64 | 62.2 | 1.26 | 0.65 | 0.0 | 0.00 | 0.00 |

TABLE 2

| Example | Oil Bath Temperature (deg C.) | Sulfuric Acid Concentration (wt % vs sorbitol) | Nitrogen Flow Rate (cm³/min) | Solvent Added | Total Reaction Time | Molar Yield Isosorbide % | Molar Yield 2,5-Anhydro-D-mannitol + 2,5-Anhydro-L-iditol (%) | Rates of Appearance and Disappearance (%/min, linear portion of curve of % vs time) Sorbitol Disappearance | Isosorbide Appearance |
|---|---|---|---|---|---|---|---|---|---|
| 1 | 180 | 0.6 | 150 | none | 35 min | 66.6 | 12.9 | 8.5 | 5.7 |
| 2 | 150 | 0.6 | 150 | none | 105 min | 70.7 | 11.3 | 3.9 | 1.2 |
| 3 | 150 | 0.6 | 450 | none | 75 min | 71.4 | 11.5 | 5.2 | 1.6 |
| 4 | 150 | 0.6 | 150 | none | 105 min | 70.7 | 11.3 | 3.9 | 1.2 |
| 5 | 150 | 0.6 | 50 | none | 120 min | 71.3 | 11.8 | 3.3 | 0.83 |
| 6 | 150 | 1.8 | 150 | none | 70 min | 71.6 | 10.8 | 6.1 | 2.4 |
| 7 | 150 | 0.6 | 150 | none | 105 min | 70.7 | 11.3 | 3.9 | 1.2 |
| 8 | 150 | 0.2 | 150 | none | 175 min | 69.6 | 11.8 | 2.3 | 0.66 |
| 9 | 100–120 | 5.4 | 500 | none | 350 min | 74.1 | 7.6 | — | — |
| 10 | 140 | 1 | 200 | Sulfolane (2:1 v:v sulfolane:sorbitol) | 70 min | 77.1 | >12.5 | — | — |

TABLE 3

| Solid Acid Catalyst | Source of Catalyst | Isosorbide Yield* | Yield Sum of 1,4- and 3,6- Anhydro-glucitols | Time (hrs) | wgt % cat. | Isosorbide Catalyst Activity** | sorbitol g (100%) | Temp | N2 Flow Rate (cc/min) | RXN Vessel Size |
|---|---|---|---|---|---|---|---|---|---|---|
| Example 11 H-beta zeolite | (Si/Al = 12.5) (CP 811BL-25, PQ Corp., Valley Forge, PA) | 18.0% | 26.4% | 5.0 | 9.3% | 0.384 | 1.495 | 150 | 450 | 7 ml vial |
| Example 12 DAY-55 zeolite | DA-Y(Si/Al = 55)(Lot # TC133, Degussa Corp., South Plainfield, NJ) | 10.0% | 30.0% | 5.1 | 9.4% | 0.209 | 1.498 | 150 | 450 | 7 ml vial |
| Example 13 H-beta zeolite | (Si/Al = 12.5) (CP 811BL-25, PQ Corp., Valley Forge, PA) | 38.0% | 1.9% | 12.3 | 20.0% | 0.155 | 9.112 | 150 | 450 | 60 ml tube |
| Example 14 Sulfated Zirconia | Synthesized in the Laboratory - Experiment 1 | 1.1% | 62.0% | 28.4 | 50.0% | 7.7E-04 | 7.524 | 150 | 450*** | 60 ml tube |
| Example 15 H-Y zeolite | (Si/Al = 25)CBV-760 Lot # 39-89-011, Conteka B. V. (now part of Zeolyst Corp., Valley Forge, PA)) | 1.3% | 21.1% | 5.1 | 9.4% | 0.027 | 1.506 | 150 | 450 | 7 ml vial |
| Example 16 H-Mordenite | (Si/Al = 45) (CBV-90A, Lot # 1822-42, Zeolyst Corp.,Valley Forge, PA) | 0.8% | 22.9% | 5.1 | 9.3% | 0.017 | 1.495 | 150 | 450 | 7 ml vial |
| Example 17 H-ZSM-5 zeolite | (Si/Al = 15) (CBV-3020, Conteka B. V. (now part of Zeolyst Corp., Valley Forge, PA)) | 0.2% | 1.5% | 5.0 | 9.4% | 0.004 | 1.495 | 150 | 450 | 7 ml vial |
| Comp Ex 18 USY xeolite | (Si/Al = 2.8) (LZ-20, Lot # 13443-7, Union Carbide Corp. (now part of UOP, DesPlaines, IL)) | 0.0% | 0.4% | 5.0 | 9.3% | 0.000 | 1.510 | 150 | 450 | 7 ml vial |
| Comp Ex 19 H-SDUSY zeolite | (Si/Al = 75) (CBV-901, Lot # 1822-66, Zeolyst Corp.,Valley Forge, PA) | 0.0% | 4.7% | 5.0 | 9.4% | 0.000 | 1.495 | 150 | 450 | 7 ml vial |
| Comp Ex 20 H-ZSM-5 zeolite | (Si/Al = 25)(CBV-5020E, Lot # 5020E-ZH-39-3, PQ Corp., Valley Forge, PA) | 0.0% | 8.9% | 5.0 | 9.4% | 0.000 | 1.496 | 150 | 450 | 7 ml vial |
| Comp Ex 21 H-ZSM-5 zeolite | (Si/Al = 75) (CBV-1502, Lot # 39 90 003, Conteka B. V. (now part of Zeolyst Corp., Valley Forge, PA)) | 0.0% | 3.2% | 5.0 | 9.5% | 0.000 | 1.499 | 150 | 450 | 7 ml vial |
| Comp Ex 22 H-Mordenite | (Si/Al = 15) (ZD-96065, Lot # 1822-41, Zeolyst Corp.,Valley Forge, PA) | 0.0% | 1.4% | 5.0 | 9.3% | 0.000 | 1.505 | 150 | 450 | 7 ml vial |
| Example 23 Sulfated Zirconia | Synthesized in the Laboratory-Experiment 1 | 73.3% | 0.1% | 1.3 | 50.0% | 1.143 | 7.536 | 170 | 450*** | 60 ml tube |

*Normalized % Isosorbide = ratio of isosorbide area/area of other products and intermediates (Where the areas are adjusted by their response factor)
**Catalyst Activity = Isosorbide Yield/Time (hrs) at which that yield was obtained/wgt % catalyst loading.
***Nitrogen was presaturated with water vapor

What is claimed is:

1. A process for the preparation of a dianhydro sugar alcohol comprising the steps of:
    a) introducing to a single vessel a charge of at least one sugar alcohol or monoanhydro sugar alcohol, and optionally, water and, optionally, a dehydration catalyst;
    b) contacting said charge with a flow of an inert gas at elevated temperature to remove the bulk of any water present to yield a dewatered process charge;
    c) contacting said dewatered process charge with a dehydration catalyst in the presence of a flow of an inert gas at elevated temperatures to remove water of reaction as formed.

2. The process of claim 1 wherein the at least one sugar alcohol is sorbitol and the product is isosorbide.

3. The process of claim 1 wherein the dehydration catalyst is sulfuric acid.

4. The process of claim 3 wherein the concentration of sulfuric acid is 0.25 to 5.0% by weight of the reaction mass.

5. The process of claim 4 wherein the concentration of sulfuric acid is 0.5 to 1.5% by weight of the reaction mass.

6. The process of claim 1 wherein the dehydration catalyst is an inorganic ion exchange material selected from the group consisting of acidic zeolites or sulfated metal oxide catalysts.

7. The process of claim 6 wherein the dehydration catalyst an acid zeolites with a minimum pore dimension (based on ionic radii of the atoms within the zeolite) of greater than or equal to 6.0 Angstroms, and a Si:Al ratio of greater than or equal to 2.8 to 1 and less than or equal to 75:1.

8. The process of claim 7 wherein the dehydration catalyst is an acid zeolite selected from the group consisting of H-beta zeolite, DA-Y zeolite, H—Y zeolite, H-Mordenite zeolite and H-ZSM-5 zeolite.

9. The process of claim 6 wherein the dehydration catalyst is sulfated zirconia.

10. The process of claim 1 conducted at a temperature of from 100–180° C.

11. The process of claim 10 conducted at a temperature of from 115–160° C.

12. The process of claim 11 conducted at a temperature of from 115–145° C.

13. The process of claim 1 wherein the inert gas is nitrogen or carbon dioxide.

14. The process of claim 13 wherein the inert gas is nitrogen.

* * * * *